United States Patent
Chen et al.

(10) Patent No.: US 10,654,766 B2
(45) Date of Patent: May 19, 2020

(54) PROCESS FOR MAKING VINYLIDENE OLEFIN

(71) Applicant: ExxonMobil Chemical Patents Inc., Baytown, TX (US)

(72) Inventors: Patrick C. Chen, Houston, TX (US); Delanyo K. Seshie, Houston, TX (US); Md Safatul Islam, Pearland, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/988,683

(22) Filed: May 24, 2018

(65) Prior Publication Data
US 2019/0062234 A1    Feb. 28, 2019

Related U.S. Application Data

(60) Provisional application No. 62/551,081, filed on Aug. 28, 2017.

(51) Int. Cl.
*C07C 2/34* (2006.01)

(52) U.S. Cl.
CPC ............ *C07C 2/34* (2013.01); *C07C 2531/14* (2013.01); *C07C 2531/22* (2013.01)

(58) Field of Classification Search
None
See application file for complete search history.

(56) References Cited

U.S. PATENT DOCUMENTS

| | | | |
|---|---|---|---|
| 3,652,655 A | 3/1972 | Fenton | |
| 4,658,078 A * | 4/1987 | Slaugh | C07C 2/04 502/117 |
| 4,658,708 A | 4/1987 | Rastoin | |
| 4,973,788 A | 11/1990 | Lin et al. | |
| 5,087,788 A | 2/1992 | Wu | |
| 5,625,106 A | 4/1997 | Marks et al. | |
| 8,119,850 B2 | 2/2012 | Fujikawa et al. | |
| 8,383,869 B2 | 2/2013 | De Kraker | |
| 8,748,361 B2 | 6/2014 | Wu et al. | |
| 2009/0069614 A1 * | 3/2009 | Yokota | C07C 2/34 585/511 |
| 2016/0017105 A1 | 1/2016 | Wu et al. | |
| 2017/0183595 A1 | 6/2017 | Ng et al. | |
| 2018/0119045 A1 | 5/2018 | Patil et al. | |

FOREIGN PATENT DOCUMENTS

| | | |
|---|---|---|
| DE | 19653829 | 6/1998 |
| EP | 1710225 | 10/2006 |
| GB | 999725 | 7/1965 |
| JP | 2004-077791 | 3/2004 |
| JP | 2005-298443 | 10/2005 |
| WO | 2014/004776 | 1/2014 |
| WO | 2017/036755 | 3/2017 |
| WO | 2017/116900 | 7/2017 |

OTHER PUBLICATIONS

U.S. Appl. No. 15/904,629, filed Feb. 26, 2018 Lewis et al.

\* cited by examiner

*Primary Examiner* — Ali Z Fadhel

(74) *Attorney, Agent, or Firm* — John R. Wright; Siwen Chen

(57) ABSTRACT

This disclosure relates to a continuous process for making a dimer from a terminal olefin in the presence of a catalyst system comprising a metallocene compound and alumoxane.

23 Claims, No Drawings

PROCESS FOR MAKING VINYLIDENE OLEFIN

PRIORITY CLAIM

This application claims priority to and the benefit of U.S. Ser. No. 62/551,081, filed Aug. 28, 2017, the content of which is incorporated by reference in its entirety.

FIELD OF THE DISCLOSURE

This disclosure relates to vinylidene olefins and processes for making them. In particular, this disclosure relates to vinylidene dimer olefins and processes for making them from a terminal olefin monomer.

BACKGROUND OF THE DISCLOSURE

Olefin compounds can be categorized into vinyls, vinylidenes, 1,2-di-substituted olefins and tri-substituted olefins depending on the substitution on the two carbon atoms connected by an ethylenic C=C bond. A vinyl olefin, represented by $RCH=CH_2$, contains one substituent R and three hydrogen atoms; a vinylidene, represented by $C(R^1R^2)=CH_2$, contains two substituents ($R^1$ and $R^2$) connected to the same carbon atom and two hydrogen atoms connected to the other carbon atom. A 1,2-di-substituted vinylene, represented by $CH(R^1)=CH(R^2)$, contains two substituents ($R^1$, $R^2$) with one connected to each carbon atom. A tri-substituted vinylene, represented by $CH(R^1)=C(R^2R^3)$, contains three substituents ($R^1$, $R^2$, $R^3$) with only one hydrogen atom left. Vinyls and vinylidenes are terminal olefins, while 1,2-di-substituted vinylenes and tri-substituted vinylenes are internal olefins. Among these four types of olefins, vinylidenes are particularly desirable due to its reactivity and are frequently used to make derivatives of the olefin for use in various applications.

Oligomeric, ethylenically unsaturated molecules made from the polymerization of terminal olefins are known. For example, U.S. Pat. No. 8,748,361 B2 discloses a mixture comprising unsaturated polyalpha-olefin ("uPAO") material made from, e.g., oligomerization of terminal olefins in the presence of metallocene catalysts. It was disclosed in this reference that the uPAOs could comprise, among others, vinyls, vinylenes, 1,2-di-substituted vinylenes, and tri-substituted vinylenes.

Recently, however, research and development in various chemical fields reveal that the ethylenically unsaturated PAO materials prepared from oligomerization of linear terminal olefins can be particularly advantageously used as intermediates for making various specialty chemicals because of the reactivity of the C=C double bond present in molecular structure of the oligomer molecules. For example, various chemical functional groups can be bonded to the carbon backbone of the uPAO molecule when a chemical agent reactive with the C=C bond is allowed to contact the uPAO material. The functional group thus introduced onto the PAO structure can bring about unique properties to the functionalized and saturated PAO molecules.

It has been found that the reactivity of the C=C bonds in vinyls, vinylidenes, 1,2-di-substituted vinylenes and tri-substituted vinylenes are different with regard to many chemical functionalization agents. For a specific type of functionalization agent, one or more particular type(s) of olefin(s) may be more desirable than the other(s). In addition, uPAOs having various molecular weight and molecular weight distribution and differing reactivities may be desired for making differing derivatives comprising differing functional groups thereon. For example, dimers of olefins as specific uPAOs can be of higher interest and value over higher oligomers such as trimers and tetramers. Furthermore, it is known that vinylidenes and tri-substituted vinylenes are more reactive than 1,2-di-substituted vinylenes with many common reagents reactive with C=C double bonds. Thus, high-purity vinylidene dimers of terminal olefins and methods for making them are of high interest.

U.S. Pat. No. 4,658,078 discloses a process for making vinylidene dimers from 1-olefins such as propylene, 1-hexene, and 1-octene by using a catalyst system comprising $bisCpZrCl_2$ and methylalumoxane. While impressive selectivity of the terminal olefin toward dimers was achieved in the examples of this patent, the oligomerization step nonetheless resulted in the formation of high quantity of trimers and higher oligomers, rendering the oligomer products from the oligomerization reaction step not directly useable as a high-purity vinylidene dimer. One would need to distill the oligomer products in order to reduce the trimers and higher oligomers to an acceptable level. Moreover, the process illustrated in this patent was a batch process, which is not efficient in producing large quantities of vinylidene dimer products. In addition, there is no teaching in this patent, particularly in the examples, of the selectivity of the 1-olefin monomers toward vinylidenes in the dimer product.

Thus, there remains a need for a process for making vinylidene olefins from terminal olefins. This disclosure satisfies this and other needs.

SUMMARY OF THE DISCLOSURE

It has been found that by using a continuous oligomerization process using a catalyst system comprising a metallocene compound such as $bisCpMX_2$ (where M can be Hf or Zr, and X can be Cl, methyl, ethyl, and the like) and alumoxane, one can produce an oligomer mixture from a terminal olefin with a selectivity of the terminal olefin toward vinylidene dimer of the terminal olefin significantly higher than those processes in the prior art, making it possible to directly use the oligomer mixture as a high-purity vinylidene dimer without the need of a step of removing trimer and other heavy oligomers from the oligomer mixture.

This disclosure relates to a continuous process for making a vinylidene dimer from a terminal olefin comprising at least four (4) carbon atoms per molecule, comprising: feeding a monomer stream comprising the terminal olefin into a reactor at a first feeding rate of R (to) moles of the terminal olefin per hour; feeding a metallocene compound having a formula $Cp(Bg)_nMX_2Cp'$ into the reactor at a second feeding rate of R(mc) moles of the metallocene compound per hour, wherein M is selected from Hf and Zr; each X is independently a halogen or a hydrocarbyl group; where Cp and Cp', the same or different, independently represents a cyclopentadienyl, alkyl-substituted cyclopentadienyl, indenyl, alkyl-substituted indenyl, 4,5,6,7-tetrahydro-2H-indenyl, alkyl-substituted 4,5,6,7-tetrahydro-2H-indenyl, 9H-fluorenyl, and alkyl-substituted 9H-fluorenyl; each Bg is a bridging group covalently linking Cp and Cp'; and n is 0, 1, or 2; feeding an alumoxane feed into the reactor at a third feeding rate corresponding to R(Al) moles of aluminum atoms per hour, wherein the alumoxane feed comprises metal elements other than aluminum, alkali metals, alkaline earth metals, and the metal contained in the metallocene compound at a total concentration no greater than 50,000 ppm by mole, based on the total moles of all metal atoms present in the alumoxane feed; conducting oligomerization reactions in the reactor at a temperature in the range from 50 to 90° C.; drawing a stream of oligomerization reaction mixture from the reactor comprising unreacted terminal olefin, a dimer of the terminal olefin, and a trimer of the terminal olefin, wherein: the first feeding rate, the second feeding rate, and the third feeding rate are chosen such that: $350 \leq R(to)/R(mc) \leq 750$, $2 \leq R(Al)/R(mc) \leq 10$, and the oligomerization reaction has a selectivity of the terminal olefin toward trimer no greater than 5%.

Further objects, features and advantages of this disclosure will be understood by reference to the following drawings and detailed description.

DETAILED DESCRIPTION OF THE DISCLOSURE

Definitions

In this disclosure, the indefinite article "a" or "an" means at least one, unless it is clearly specified or indicated by the context to mean one.

The term "alkyl group" or "alkyl" interchangeably refers to a saturated hydrocarbyl group consisting of carbon and hydrogen atoms. "Linear alkyl group" refers to a non-cyclic alkyl group in which all carbon atoms are covalently connected to no more than two carbon atoms. "Branched alkyl group" refers to a non-cyclic alkyl group in which at least one carbon atom is covalently connected to more than two carbon atoms. "Cycloalkyl group" refers to an alkyl group in which all carbon atoms form a ring structure comprising one or more rings.

The term "aryl group" refers to an unsaturated, cyclic hydrocarbyl group consisting of carbon and hydrogen atoms in which the carbon atoms join to form a conjugated π system. Non-limiting examples of aryl groups include phenyl, 1-naphthyl, 2-naphthyl, 3-naphthyl, and the like.

The term "arylalkyl group" refers to an alkyl group substituted by an aryl group or alkylaryl group. Nonelimiting examples of arylalkyl group include benzyl, 2-phenylpropyl, 4-phenylbutyl, 3-(3-methylphenyl)propyl, 3-(p-tolyl)propyl, and the like.

The term "alkylaryl group" refers to an aryl group substituted by an alkyl group. Non-limiting examples of alkylaryl group include 2-methylphenyl, 3-methylphenyl, 4-methylphenyl, 2-methyl-1-naphthyl, 6-phenylhexyl, 5-pentylphenyl, 4-butylphenyl, 4-tert-butylphenyl, 7-phenylheptanyl, 4-octylphenyl, and the like.

The term "cycloalkylalkyl group" refers to an alkyl group substituted by a cycloalkyl group or an alkylcycloalkyl group. An example of cycloalkylalkyl group is cyclohexylmethyl.

The term "alkylcycloalkyl group" refers to a cycloalkyl group substituted by an alkyl group. Non-limiting examples of alkylcycloalkyl group include 2-methylcyclohexyl, 3-methylcyclohexyl, 4-methylcyclohexyl, 4-tert-butyl cyclohexyl, 4-phenylcyclohexyl, cyclohexylpentyl, and the like.

The term "Hydrocarbyl group" or "hydrocarbyl" interchangeably refers to a group consisting of hydrogen and carbon atoms only. A hydrocarbyl group can be saturated or unsaturated, linear or branched, cyclic or acyclic, containing a cyclic structure or free of cyclic structure, and aromatic or non-aromatic.

"Cn" group or compound refers to a group or a compound comprising carbon atoms at total number thereof of n. Thus, "Cm-Cn" or "Cm to Cn" group or compound refers to a group or compound comprising carbon atoms at a total number thereof in the range from m to n. Thus, a C1-C50 alkyl group refers to an alkyl group comprising carbon atoms at a total number thereof in the range from 1 to 50.

The term "carbon backbone" in an alkane or an alkyl group refers to the longest straight carbon chain in the molecule of the compound or the group in question.

The term "carbon backbone" of an olefin is defined as the straight carbon chain therein including a C=C functionality having the largest number of carbon atoms.

The term "olefin" refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be linear, branched linear, or cyclic.

The term "terminal olefin" refers to an olefin having a terminal carbon-to-carbon double bond in the structure thereof $((R^1R^2)-C=CH_2$, where $R^1$ and $R^2$ can be independently hydrogen or any hydrocarbyl group, preferably $R^1$ is hydrogen, and $R^2$ is an alkyl group). A "linear terminal olefin" is a terminal olefin defined in this paragraph wherein $R^1$ is hydrogen, and $R^2$ is hydrogen or a linear alkyl group.

The term "vinyl" means an olefin having the following formula:

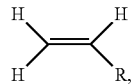

wherein R is a hydrocarbyl group, preferably a saturated hydrocarbyl group such as an alkyl group.

The term "vinylidene" means an olefin having the following formula:

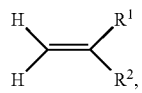

wherein $R^1$ and $R^2$ are each independently a hydrocarbyl group, preferably a saturated hydrocarbyl group such as alkyl group.

The term "1,2-di-substituted vinylene" means
(i) an olefin having the following formula:

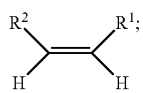

or
(ii) an olefin having the following formula:

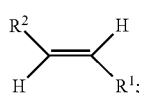

or
(iii) a mixture of (i) and (ii) at any proportion thereof, wherein $R^1$ and $R^2$, the same or different at each occurrence, are each independently a hydrocarbyl group, preferably saturated hydrocarbyl group such as alkyl group.

The term "tri-substituted vinylene" means an olefin having the following formula:

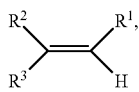

wherein $R^1$, $R^2$, and $R^3$ are each independently a hydrocarbyl group, preferably a saturated hydrocarbyl group such as alkyl group.

The term "polyalpha-olefin(s)" ("PAO(s)") includes any oligomer(s) and polymer(s) of one or more terminal olefin monomer(s). PAOs are oligomeric or polymeric molecules produced from the polymerization reactions of terminal olefin monomer molecules in the presence of a catalyst system, optionally further hydrogenated to remove residual carbon-carbon double bonds therein. Thus, the PAO can be a dimer (resulting from two terminal olefin molecules), a trimer (resulting from three terminal olefin molecules), a tetramer (resulting from four terminal olefin molecules), or any other oligomer or polymer comprising two or more structure units derived from one or more terminal olefin monomer(s). The PAO molecule can be highly regio-regular, such that the bulk material exhibits an isotacticity, or a syndiotacticity when measured by $^{13}C$ NMR. The PAO molecule can be highly regio-irregular, such that the bulk material is substantially atactic when measured by $^{13}C$ NMR. A PAO material made by using a metallocene-based catalyst system is typically called a metallocene-PAO ("mPAO"), and a PAO material made by using traditional non-metallocene-based catalysts (e.g., Lewis acids, supported chromium oxide, and the like) is typically called a conventional PAO ("cPAO"). A PAO material that has not been hydrogenated and therefore is unsaturated is called an unhydrogenated PAO ("uPAO").

The term "selectivity" of a terminal olefin in a reaction toward a given product species means the percentage of the terminal olefin converted into the given product species on the basis of the all of the terminal olefin converted. Thus, if in a specific oligomerization reaction, 5% of the terminal olefin monomer is converted into trimer, then the selectivity of the terminal olefin toward trimer in the oligomerization reaction is 5%.

In this disclosure, all molecular weight data are in the unit of grams per mole ($g \cdot mol^{-1}$).

NMR spectroscopy provides key structural information about the synthesized polymers. Proton NMR ($^1$H-NMR) analysis of the unsaturated PAO product gives a quantitative breakdown of the olefinic structure types (viz. vinyl, 1,2-di-substituted, tri-substituted, and vinylidene). In this disclosure, compositions of mixtures of olefins comprising terminal olefins (vinyls and vinylidenes) and internal olefins (1,2-di-substituted vinylenes and tri-substituted vinylenes) are determined by using $^1$H-NMR. Specifically, a NMR instrument of at least a 500 MHz is run under the following conditions: a 30° flip angle RF pulse, 120 scans, with a delay of 5 seconds between pulses; sample dissolved in $CDCl_3$ (deuterated chloroform); and signal collection temperature at 25° C. The following approach is taken in determining the concentrations of the various olefins among all of the olefins from an NMR spectrum. First, peaks corresponding to different types of hydrogen atoms in vinyls (T1), vinylidenes (T2), 1,2-di-substituted vinylenes (T3), and tri-substituted vinylenes (T4) are identified at the peak regions in TABLE I below. Second, areas of each of the above peaks (A1, A2, A3, and A4, respectively) are then integrated. Third, quantities of each type of olefins (Q1, Q2, Q3, and Q4, respectively) in moles are calculated (as A1/2, A2/2, A3/2, and A4, respectively). Fourth, the total quantity of all olefins (Qt) in moles is calculated as the sum total of all four types (Qt=Q1+Q2+Q3+Q4). Finally, the molar concentrations (C1, C2, C3, and C4, respectively, in mol %) of each type of olefin, on the basis of the total molar quantity of all of the olefins, is then calculated (in each case, Ci=100*Qi/Qt).

TABLE I

| Hydrogen Atoms | | Peak Region (ppm) | Peak Area | Number of Hydrogen Atoms | Quantity of Olefin (mol) | Concentration of Olefin (mol %) |
|---|---|---|---|---|---|---|
| Type No. | Olefin Structure | | | | | |
| T1 | $CH_2$=CH—$R^1$ | 4.95-5.10 | A1 | 2 | Q1 = A1/2 | C1 |
| T2 | $CH_2$=$CR^1R^2$ | 4.70-4.84 | A2 | 2 | Q2 = A2/2 | C2 |
| T3 | $CHR^1$=$CHR^2$ | 5.31-5.55 | A3 | 2 | Q3 = A3/2 | C3 |
| T4 | $CR^1R^2$=CH $R^3$ | 5.11-5.30 | A4 | 1 | Q4 = A4 | C4 |

All percentages in describing chemical compositions herein are by weight unless specified otherwise. "wt %" means percent by weight.

"Consisting essentially of" means comprising at a concentration by weight of at least 90 wt %, based on the total weight of the mixture in question. Thus, an oligomerization product mixture consisting essentially of a dimer comprises dimer at a concentration by weight of at least 90 wt %, based on the total weight of the oligomerization product mixture.

All numerical values within the detailed description and the claims herein are modified by "about" or "approximately" the indicated value, taking into account experimental error and variations that would be expected by a person having ordinary skill in the art.

All kinematic viscosity values in this disclosure are as determined pursuant to ASTM D445. Kinematic viscosity at 100° C. is reported herein as KV100, and kinematic viscosity at 40° C. is reported herein as KV40. Unit of all KV100 and KV40 values herein is cSt unless otherwise specified.

All viscosity index ("VI") values in this disclosure are as determined pursuant to ASTM D2270.

The process for making a dimer from a terminal olefin feed of this disclosure is continuous, as opposed to a batch process such as those disclosed in U.S. Pat. No. 4,658,078. The oligomerization (dimerization being one) reaction can therefore be carried out in a continuously operated reactor, such as a continuously stirred tank reactor, a plug flow reactor or a loop reactor. Quite surprisingly, it was found that in a continuous process, one can achieve an extremely high selectivity of the terminal olefin toward dimer of the terminal olefin monomer and avoid the production of high quantity of trimer and higher oligomer.

This continuous process represents a significant improvement to the processes disclosed in U.S. Pat. No. 4,658,078, as it results in the production of a high-purity vinylidene olefin dimer of the terminal olefin dimer. The oligomerization reaction pursuant to the continuous process features an exceedingly high selectivity toward dimer and exceedingly low selectivity toward trimers and higher oligomers and an exceedingly high selectivity toward vinylidene olefin dimer as opposed to 1,2-di-substituted vinylene and tri-substituted vinylene. Thus, the oligomer mixture obtained from the oligomerization step, upon removal of residual terminal olefin monomer and catalyst, can be used directly as a high-purity vinylidene olefin dimer for its intended purpose. In addition, the oligomerization reaction can be carried out with a high conversion of the terminal olefin monomer. Moreover, the oligomerization reaction of the continuous process results in little isomerization of the terminal olefin monomer, the dimer, and other oligomers. Therefore, the residual terminal olefin monomer contained in the oligomerization reaction mixture can be separated and recycled to the oligomerization reaction. Last but not least, the oligomerization reaction in the continuous process is carried out under mild, steady conditions in a continuous fashion, resulting in a vinylidene olefin dimer with consistent composition and quality, which, in turn, can be used for making a derivative thereof with high purity.

I. The Terminal Olefin

The terminal olefin monomer useful in the process of this disclosure can desirably comprise from n1 to n2 carbon atoms per molecule, where n1 and n2 can be, independently, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, 60, as long as n1<n2. Preferably n1=4 and n2=50; more preferably n1=6 and n2=40; still more preferably n1=6 and n2=30; still more preferably n1=6 and n2=20.

Preferred terminal olefin monomers are mono-olefins containing one C=C bond per monomer molecule, though those olefins containing two or more C=C bonds per monomer molecule can be used as well.

The terminal olefin monomer useful in the process of this disclosure can be preferably a linear terminal olefin. Particularly useful examples of linear terminal olefins as the monomer for the process of this disclosure are: 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-icosene, 1-henicosene, 1-docosene, 1-tricosene, 1-tetracosene, 1-pentacosene, 1-hexacosene, 1-heptacosene, 1-octacosene, 1-nonacosene, and 1-triacontene. Preferred examples of linear terminal olefins as the monomer for the process of this disclosure are: 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-icosene. Still more preferred linear terminal olefin as monomer for the process of this disclosure are: 1-pentene, 1-hexene, 1-octene, 1-decene, 1-dodecene, 1-tetradecene, 1-hexadecene, 1-octadecene, and 1-icosene. Still more preferred linear terminal olefins as monomer for the process of this disclosure are: 1-hexene, 1-octene, 1-decene, 1-dodecene, 1-tetradecene, 1-hexadecene, and 1-octadecene. Linear terminal olefins having even number of carbon atoms can be advantageously manufactured by the oligomerization of ethylene, as is typically done in the industry. Many of these linear terminal olefins with even number of carbon atoms are commercially available at large quantities.

Branched terminal olefins can be used as the monomer in the process as well. Particularly useful branched terminal olefins are those represented by the following formula:

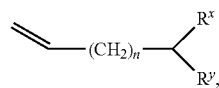

where $R^x$ and $R^y$ are independently any hydrocarbyl group, preferably any C1-C30 alkyl group, more preferably any C1-C30 linear alkyl group, n is an integer, and n≥2, preferably n≥4, more preferably n≥5. Preferably n≤30, more preferably n≤20, still more preferably n≤15.

The terminal olefin monomer may be fed as a pure material or as a solution in an inert solvent into the continuously operated oligomerization reactor. Non-limiting examples of the inert solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

The terminal olefins used herein can be produced directly from ethylene growth process as practiced by several commercial production processes, or they can be produced from Fischer-Tropsch hydrocarbon synthesis from $CO/H_2$ syngas, or from metathesis of internal olefins with ethylene, or from cracking of petroleum or Fischer-Tropsch synthetic wax at high temperature, or any other terminal olefin synthesis routes. A preferred feed for this invention is preferably at least 80 wt % terminal olefin (preferably linear alpha olefin), preferably at least 90 wt % terminal olefin (preferably linear alpha olefin), more preferably 100% terminal olefin (preferably linear alpha olefin). The feed olefins can be the mixture of olefins produced from other linear terminal olefin process containing C4 to C20 terminal olefins as described in Chapter 3 "Routes to Alpha-Olefins" of the book Alpha Olefins Applications Handbook, Edited by G. R. Lappin and J. D. Sauer, published by Marcel Dekker, Inc. N.Y. 1989.

The terminal olefin feed and or solvents may be treated to remove catalyst poisons, such as peroxides, oxygen or nitrogen-containing organic compounds or acetylenic compounds before being supplied to the polymerization reactor. The treatment of the linear terminal olefin with an activated 13 Angstrom molecular sieve and a de-oxygenate catalyst, i.e., a reduced copper catalyst, can increase catalyst productivity (expressed in terms of quantity of PAO produced per micromole of the metallocene compound used) more than 10-fold. Alternatively, the feed olefins and or solvents are treated with an activated molecular sieve, such as 3 Angstrom, 4 Angstrom, 8 Angstrom or 13 Angstrom molecular sieve, and/or in combination with an activated alumina or an activated de-oxygenated catalyst. Such treatment can desirably increase catalyst productivity 2- to 10-fold or more.

Where a substantially pure dimer compound

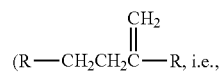

a vinylidene olefin where the two $R^1$ groups are identical) is desirable, a single terminal olefin monomer ($R$—$CH$=$CH_2$) can be fed into the oligomerization reactor. Thus, a pure 1-octene feed will result in a single C16 dimer vinylidene olefin (7-methylenepentadecane), a pure 1-decene feed will result in a single C20 dimer vinylidene olefin (9-methylenenonadecane), a pure 1-dodecene feed will result in a single C24 dimer vinylidene olefin (11-methylenetricosane), a pure 1-tetradecene feed will result in a single C28 dimer vinylidene olefin (13-methyleneheptacosane).

If two different terminal olefin monomers including a first monomer ($R^a$—$CH$=$CH_2$) and a second monomer ($R^b$—$CH$=$CH_2$, where $R^b$ differs from $R^a$) are fed into the oligomerization reactor, multiple different dimer compounds may be produced at various quantities depending on the dimerization reactivity of them: a first dimer formed from two units of the first monomer

corresponding to a vinylidene olefin where the two $R^1$ groups are identical $R^a$); a second dimer formed from two units of the second monomer

corresponding to a vinylidene olefin where the two $R^1$ groups are identical $R^b$), and a third category of dimers formed from one unit of the first monomer and another unit of the second monomer

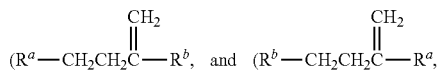

corresponding to vinylidene olefins having formula (F-II) where the two $R^1$ groups are different). The third category of dimers can have multiple isomers as shown. By way of example, a terminal olefin feed consisting of 1-decene and 1-dodecene in the process of this disclosure results in the production of a dimer mixture comprising 9-methylenenonadecane, 9-methylenehenicosane, 11-methylenehenicosane, and 11-methylenetricosane. To the extent such a dimer mixture is acceptable for the intended application, a mixture of two (or even more) terminal olefin may be used as a terminal olefin feed into the oligomerization reactor. In commercial productions, even a high-purity terminal olefin feed invariably contains impurities such as other terminal olefins at various concentrations in addition to the predominant terminal olefin. As a result, various quantities of multiple minor vinylidene olefin dimer olefins may be produced in addition to the intended predominant dimer of the predominant terminal olefin. To the extent the presence of such minor vinylidene dimer olefins at the specific quantities does not interfere with the intended use of the dimer product, such terminal olefin feed comprising minor quantities of other terminal olefin(s) than the predominant terminal olefin can be tolerated in the process of this disclosure.

It is highly desirable that the terminal olefin monomer feed consists essentially of a single terminal olefin. It is contemplated that the monomer feed may comprise multiple terminal olefins having differing formulas and/or molecular weight. In such case, as discussed above, multiple vinylidene olefins having different formulas may be produced in the dimerization reaction, which can be used together as a vinylidene olefin product as is. Where the monomer feed comprises multiple terminal olefins, it is highly desirable that they differ in terms of molecular weight thereof by no greater than 145 (or 130, 115, 100, 85, 70, 55, 45, 30, or even 15) grams per mole. Preferably in such cases the multiple terminal olefins contained in the monomer feed differ in terms of total number of carbon atoms contained therein by no greater than 10 (or 9, 8, 7, 6, 5, 4, 3, 2, or even 1).

II. The Metallocene Compound

The metallocene compound in the catalyst system useful in the continuous process of this disclosure can be represented by the formula $Cp(Bg)_nMX_2Cp'$, where Cp and Cp', the same or different, represents a cyclopentadienyl, alkyl-substituted cyclopentadienyl, indenyl, alkyl-substituted indenyl, 4,5,6,7-tetrahydro-2H-indenyl, alkyl-substituted 4,5,6,7-tetrahydro-2H-indenyl, 9H-fluorenyl, and alkyl-substituted 9H-fluorenyl; Bg represents a bridging group covalently linking Cp and Cp', and n is zero (0), one (1), or two (2), preferably zero (0) or one (1), more preferably zero (0, i.e., where the metallocene compound is unbridged). Exemplary Bg can be represented by any of

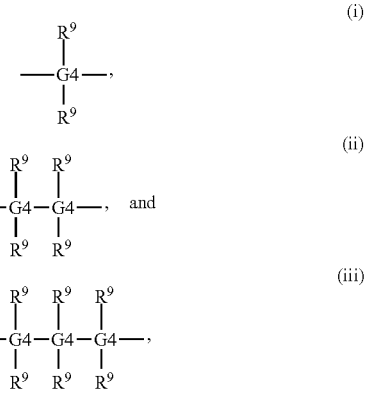

where groups G4 are, the same or different at each occurrence, independently selected from carbon, silicon, and germanium, and each $R^9$ is independently a C1-C30 substituted or unsubstituted linear, branched, or cyclic hydrocarbyl groups. Preferred $R^9$ includes substituted or unsubstituted methyl, ethyl, n-propyl, phenyl, and benzyl. Preferably Bg is category (i) or (ii) above. More preferably Bg is category (i) above. Preferably all $R^9$'s are identical.

M represents Hf or Zr. Preferably M is Zr. X, the same or different at each occurrence, independently represents a halogen such as Cl or a hydrocarbyl such as: linear or branched alkyl group such as methyl, ethyl, n-propyl, isopropyl, n-butyl and branched isomeric group thereof, n-pentyl and branched isomeric group thereof, n-hexyl and branched isomeric group thereof, n-heptyl and branched isomeric group thereof, n-octyl and branched isomeric group thereof, n-nonyl and branched isomeric group thereof, n-decyl and branched isomeric group thereof, and the like; a cycloalkyl group; a cycloalkylalkyl group; an alkylcycloalkyl group; an aryl group such as phenyl; an arylalkyl group such as benzyl; an alkylaryl group such as tolyl and xylyl. Preferably X is methyl or Cl; more preferably X is Cl. Without intending to be bound by a particular theory, it is believed that the use of the metallocene compound results in the formation of vinylidene olefin in the oligomerization reaction. A more preferred group of metallocene compound useful for the continuous process for making the vinylidene olefin used in the process for making gamma-branched alcohol product of this disclosure are those unbridged metallocene compounds having a general formula bisCpMX$_2$, where bisCp represents two cyclopentadienyl rings, M is Zr or Hf (preferably Zr), and X is as defined above, but preferably selected from Cl, C1-C10 linear or branched alkyl groups, phenyl, and benzyl. The most preferred metallocene compound useful in the continuous process for making the vinylidene olefin having formula (F-II) is bis-CpZrCl$_2$, which is commercially available and can be represented by the following formula:

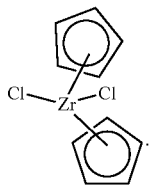

In the continuous process of this disclosure, the terminal olefin monomer (or multiple co-monomers) are fed into the oligomerization reactor at a first feeding rate of R(to) moles per hour, and the metallocene compound is fed into the reactor at a second feeding rate of R(mc) moles per hour. To achieve a high conversion of the terminal olefin monomer and a low selectivity of the terminal olefin toward trimer of the monomer of at most 5% (hence a high selectivity of the terminal olefin toward dimer) in the oligomerization reaction, it is highly desirable that the ratio of the first feeding rate to the second feeding rate R(to)/R(mc) be in the range from x1 to x2, where x1 and x2 can be, independently, 100, 150, 200, 250, 300, 350, 400, 450, 500, 550, 600, 650, 700, 750, 800, 850, 900, 950, or 1,000, as long as x1<x2. Preferably x1=300, and x2=800. More preferably x1=400, and x2=750. Still more preferably x1=500, and x2=750. If the ratio of R(to)/R(mc) is higher than 1,000, the conversion of the terminal olefin monomer in the oligomerization reaction can be too low. If the ratio of R(to)/R(mc) is lower than 100, the consumption of the metallocene compound can be too large, which is also undesirable.

It is highly desirable that the metallocene compound is dissolved or dispersed in an inert solvent and then fed into the reactor as a solution or a dispersion. Such inert solvent for the metallocene compound can be, e.g., benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

One or more metallocene compound(s) may be used in the continuous process of this disclosure.

III. The Alumoxane Feed

The alumoxane used in the process of this disclosure functions as activator of the metallocene compound and scavenger for impurities (such as water). Alumoxanes can be obtained by partial hydrolysis of alkyl aluminum compounds. Thus, non-limiting examples of alumoxanes useful in the process of this disclosure include those made by partial hydrolysis of trimethyl aluminum, triethyl aluminum, tri(n-propyl)aluminum, tri(isopropyl)aluminum, tri(n-butyl) aluminum, tri(isobutyl)aluminum, tri-(tert-butyl)aluminum, tri(n-pentyl)aluminum, tri(n-hexyl)aluminum, tri(n-octyl) aluminum, and mixtures thereof. Preferred alumoxane for the process of this disclosure is methylalumoxane ("MAO") made from partial hydrolysis of trimethyl aluminum.

The alumoxane feed supplied into the continuously operated oligomerization reactor is advantageously substantially free of metal elements other than aluminum, alkali metals, alkaline earth metals, and the metal(s) contained in the metallocene compound(s) described above. Preferably, the alumoxane feed used in the process of this disclosure comprises metal elements other than aluminum, alkali metals, alkaline earth metals, Zr, and Hf at a total concentration of no greater than x1 ppm by mole, based on the total moles of all metal atoms in the alumoxane feed, where x1 can be 50,000, 40,000, 30,000, 20,000, 10,000, 8,000, 6,000, 5,000, 4,000, 2,000, 1,000, 800, 600, 500, 400, 200, 100, 80, 60, 50, 40, 20, or even 10. More preferably, the alumoxane feed used in the process of this disclosure comprises metal elements other than aluminum, Zr, and Hf at a total concentration of no greater than x2 ppm by mole, based on the total moles of all metal atoms in the alumoxane feed, where x2 can be 50,000, 40,000, 30,000, 20,000, 10,000, 8,000, 6,000, 5,000, 4,000, 2,000, 1,000, 800, 600, 500, 400, 200, 100, 80, 60, 50, 40, 20, or even 10. Still more preferably, the alumoxane feed fed into the reactor is free of all metals other than aluminum and the metal(s) contained in the metallocene compound(s) described above. Ions or compounds of metal elements other than aluminum, alkali metals and alkaline earth metals can be Lewis acids capable of catalyzing undesired polymerization of the terminal olefin monomer, the dimer and higher oligomers, resulting in the production of undesired 1,2-di-substituted vinylenes and tri-substituted vinylenes. Lewis acids such as metal ions can also catalyze the isomerization of the terminal olefin monomer and the isomerization of the vinylidene olefin dimer and higher oligomers, resulting in the production of internal olefin isomers of the terminal olefin monomer, 1,2-di-substituted vinylene and tri-substituted vinylene dimers and higher oligomers, which is undesirable for many applications of the oligomer product, including but not limited to the dimer product.

Preferably the alumoxane used in the continuous process of this disclosure is substantially free of any Lewis acid capable of catalyzing the isomerization of the terminal olefin monomer, isomerization of a vinylidene olefin dimer, and polymerization of the terminal olefin monomer via mechanism differing from the oligomerization catalyzed by the metallocene compound used herein. For the purpose of this disclosure, the metallocene compound per se, the alumoxane per se, and any variations and derivatives thereof during the oligomerization reaction are not considered as Lewis acids.

A portion or the entirety of the alumoxane fed into the continuously operated oligomer reactor may be mixed with a portion or the entirety of the metallocene compound(s) described above, preferably dissolved and/or dispersed into an inert solvent, before it is fed into the reactor. In such case, the stream carrying a portion or the entirety of alumoxane fed into the reactor may contain the metal element(s) contained in the metallocene compound(s).

The alumoxane may be supplied into the reactor as a stream separate from the terminal olefin monomer stream and the metallocene compound stream. Alternatively or in addition, at least a portion of the alumoxane may be combined with the terminal olefin monomer and supplied into the reactor together. Mixing alumoxane with the olefin monomer before being supplied into the reactor can result in the scavenging of catalyst poisons contained in the monomer feed before such poisons have a chance to contact the metallocene compound inside the reactor. It is also possible to combine at least a portion of the alumoxane with at least a portion of the metallocene compound in a mixture, and supply the mixture as a catalyst stream into the reactor.

The alumoxane is desirably dissolved or dispersed in an inert solvent before being fed into the reactor or before being combined with the monomer feed and/or the metallocene compound. Mention of non-limiting examples of such inert solvent can be made of the following: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

IV. Oligomerization Reaction Conditions

In the continuous process of this disclosure, the terminal olefin monomer (or multiple co-monomers) is fed into the oligomerization reactor at a first feeding rate of R(to) moles per hour, and the metallocene compound is fed into the reactor at a second feeding rate of R(mc) moles per hour, and the alumoxane is fed into the reactor at a third feeding rate corresponding to R(Al) moles of aluminum atoms per hour.

To achieve a high conversion of the terminal olefin monomer and a low selectivity of the terminal olefin toward trimer of the monomer of at most 5% (hence a high selectivity of the terminal olefin toward dimer) in the oligomerization reaction, it is highly desirable that the ratio of the third feeding rate to the second feeding rate R(Al)/R(mc) be in the range from y1 to y2, where y1 and y2 can be, independently, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, as long as y1<y2. Preferably y1=2.0, and y2=12.0. More preferably y1=2.0, and y2=10.0. Still more preferably y1=2.0, and y2=7.0. Still more preferably y1=2.0, and y2=5.0. If the ratio of R(Al)/R(mc) is higher than 15.0, selectivity of the terminal olefin toward trimer and higher oligomers can be too high. If the ratio of R(Al)/R(mc) is lower than 1.0, the conversion of the terminal olefin monomer in the oligomerization reaction can be too low.

The oligomerization reaction in the process of this disclosure advantageously is carried out at a mild temperature in the range from t1 to t2° C., where t1 and t2 can be, independently, 30, 35, 40, 45, 50, 55, 60, 65, 70, 75, 80, 85, or 90, as long as t1<t2. Preferably t1=40, and t2=80. More preferably t1=50, and t2=75. If the temperature is below 30° C., the reaction kinetics can be too slow. If the temperature is higher than 90° C., selectivity of the terminal olefin toward trimer and higher oligomers can be too high and the catalyst activity may be too low.

The oligomerization reaction may be carried out at a residence time in the range from rt1 to rt2 hours, where rt1 and rt2 can be, independently, 1.0, 1.5, 2.0, 2.5, 3.0, 3.5, 4.0, 4.5, 5.0, 5.5, 6.0, 6.5, 7.0, 7.5, 8.0, 8.5, 9.0, 9.0, 10, 12, 15, 18, 24, 30, 36, 42, or 48, as long as rt1<rt2. Preferably rt1=3 and rt2=8. More preferably rt1=4 and rt2=8. Still more preferably rt1=5 and rt2=7.

The oligomerization reaction is preferably carried out in the presence of mechanical stirring of the reaction mixture such that a substantially homogeneous reaction mixture with a steady composition is withdrawn from the reactor once the reactor reaches steady state.

Advantageously the oligomerization reaction of the process of this disclosure is carried out under mild pressure. Because the oligomerization reaction is sensitive to water and oxygen, the reactor is typically protected by an inert gas atmosphere such as nitrogen. To prevent air leakage into the reactor, it is desirable that the total pressure inside the reactor is slightly higher than the ambient pressure.

The oligomerization reaction can be carried out in the presence of a quantity of inner solvent. Non-limiting examples of such solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

Due to the nature of the metallocene compound and the alumoxane used in the process of this disclosure, in the oligomerization reaction, a high selectivity of the terminal olefin toward vinylidenes olefins (e.g., at least 95%, 96%, 97%, 98%, or even 99%) and a low selectivity of the terminal olefin toward internal olefins including 1,2-di-substituted vinylenes and tri-substituted vinylenes (e.g., at most 5%, 4%, 3%, 2%, or even 1%) can be achieved. Thus, the oligomers thus made, especially the dimer, tend to be predominantly vinylidene and can be advantageously used as a vinylidene without further purification in applications where vinylidenes are desired.

As a result of the use of a continuous process, and the use of a metallocene compound and an alumoxane in the respective quantities above, we were able to achieve extremely low selectivity of the terminal olefin of the terminal olefin monomer toward trimer in the oligomerization reaction of at most 5%, thereby achieving a high selectivity of the terminal olefin toward the intended dimer. In certain embodiments, selectivity of the terminal olefin toward trimer can reach no greater than 4%, no greater than 3%, no greater than 2%, or even no greater than 1%. At such low selectivity of the terminal olefin toward trimer, selectivity of the terminal olefin toward tetramer and even higher oligomers are even lower and in many embodiments negligible. Thus, in the oligomerization reaction of the process of this disclosure, the selectivity of the terminal olefin toward tetramer and higher oligomers is typically no greater than 2%, or no greater than 1%, or no greater than 0.5%, or even no greater than 0.1%. Thus, in the oligomerization reaction of the process of this disclosure, the selectivity of the terminal olefin toward dimer can be at least 90% (or ≥91%, ≥92%, ≥93%, ≥94%, ≥95%, ≥96%, ≥97%, ≥98%, or even ≥99%).

In addition to the high selectivity of the terminal olefin monomer toward dimer in the oligomerization reaction, the process of this disclosure also exhibits a high conversion of the terminal olefin monomer, e.g., a conversion of at least 40%, 45%, 50%, 55%, 60%, 65%, or 70%, can be achieved in a single pass oligomerization reaction. With recycling of unreacted monomer separated from the oligomerization reaction mixture to the oligomerization reactor, the overall conversion can be even higher, making the process of this disclosure particular economic.

Because the alumoxane introduced into the reaction system in the process of this disclosure is substantially free of metals other than aluminum, metals contained in the metallocene compound, alkali metals, and alkaline earth metals, the terminal olefin monomer does not undergo significant isomerization reaction. Likewise, the isomerization of the vinylidene dimers and higher oligomers to form 1,2-disubstituted vinylene and tri-substituted vinylene is substantially avoided as well.

V. Post-Oligomerization Treatment

The oligomerization reaction mixture stream withdrawn from the reactor typically comprises the unreacted terminal olefin monomer, the intended dimer, trimer, tetramer and higher oligomers, the metallocene compound, the alumoxane, and optional solvent.

Once the oligomerization reaction mixture stream leaves the reactor, typically a stream of quenching agent is injected into the stream to terminate the oligomerization reactions. Non-limiting examples of quenching agents include: water, alcohols such as methanol and ethanol, CO2, and mixtures thereof. A particularly desirable quenching agent is water.

The metal elements contained in the oligomerization mixture, including aluminum and Zr or Hf, needs to be removed from the mixture. Removal thereof can be achieved through mechanical filtration using a filtration aid such as Celite. Presence of aluminum in the liquid mixture can cause isomerization of the monomer and dimer during subsequently processing steps, such as distillation to remove the unreacted monomers and the optional distillation to remove higher oligomers such as trimers and tetramers in rare cases where the purity requirement for the dimer is so high that even the small quantity of trimer and higher oligomers produced in the continuous process of this disclosure is considered excessive. It is highly desirable that upon filtration, the liquid mixture contains aluminum at a concentration no higher than 50 ppm by weight (preferably no higher than 30 ppm, still more preferably no higher than 20 ppm, still more preferably no higher than 10, still preferably no higher than 5 ppm), based on the total weight of the liquid mixture.

Upon filtration, a mixture comprising monomer, the desired dimer, the trimer and higher oligomers and the optional solvent is obtained. The monomer and solvent can be removed by flashing or distillation at an elevated temperature and/or optionally under vacuum. Because isomerization of the monomer is avoided in (i) in the oligomerization reaction due to the lack of Lewis acid capable of catalyzing isomerization reaction, and (ii) in the flashing/distillation step due to the removal of aluminum and other metal elements from the liquid mixture at the earlier filtration step, the monomer reclaimed form the mixture consists essentially of the terminal olefin monomer as introduced into the reactor. As such, the reclaimed monomer can be recycled to the oligomerization reactor as a portion of the monomer stream. The thus obtained oligomer mixture absent monomer and solvent may be used as a vinylidene dimer olefin product as is due to the low percentage of trimer and higher oligomers. For certain applications where even higher purity of the dimer is desirable, one can remove the timer and higher oligomers by further separation such as distillation.

VI. The Vinylidene Dimer Product

The dimer product as a result of the continuous process for making the vinylidene olefin having formula (F-II) advantageous comprises dimer(s) of the monomer(s) as the predominant component, trimers at a concentration no higher than 5 wt % (preferably ≤4 wt %, ≤3 wt %, ≤2 wt %, ≤1 wt %, or even ≤0.5 wt %), based on the total weight of the dimer product.

The dimer product as a result of the continuous process for making the vinylidene olefin having formula (F-II) can advantageously comprise vinylidene(s) at a total concentration of at least 95 wt % (preferably ≥96 wt %, ≥97 wt %, ≥98%, or even ≥99 wt %), based on the total weight of the dimer product.

The vinylidene dimer product obtainable from the process of this disclosure can advantageously comprise one of the following compounds at a concentration of at least 95 wt %, at least 96 wt %, at least 97 wt %, at least 98 wt %, or even at least 99 wt %, based on the total weight of the dimer product, if a substantially pure terminal olefin (with a concentration of at least 95 wt %, 96 wt %, 97 wt %, 98 wt %, or 99 wt % of the terminal olefin, based on the total weight of the terminal olefins included in the monomer feed) is utilized as the monomer feed: 3-methylenepentane (from 1-butene); 4-methylenenonane (from 1-pentene); 5-methyleneundecane (from 1-hexene); 6-methylenetridecane (from 1-heptene); 7-methylenepentadecane (from 1-octene); 8-methyleneheptadecane (from 1-nonene); 9-methylenenonadecane (from 1-decene); 11-methylenetricosane (from 1-dodecene); 13-methyleneheptacosane (from 1-tetradecene); 15-methylenehentriacontane (from 1-hexadecene); 17-methyleneheptatriacontane (from 1-octadecene); and 19-methylenenonatriacontane (from 1-iscocene).

The high-purity, predominantly dimer, predominantly vinylidene product resulting from the continuous process for making the vinylidene olefin having formula (F-II) can then be advantageously used as is as a high-purity organic compound in many applications.

The dimer product per se is a wax if it contains carbon atoms at a total number per molecule of at least, e.g., 20. It can therefore be used as a wax. Alternatively, such a waxy dimer may be hydrogenated to form a paraffin wax and then used as such.

The present invention is further illustrated by the following non-limiting examples.

EXAMPLES

Example 1: Dimerization of 1-Tetradecene in a Continuous Reactor

Into a 2-gallon (6.56-liter) continuously stirred tank reactor was continuously fed 1-tetradecene feed (containing 98.6 wt % 1-tetradecene, 0.7 wt % 1-dodecene and 0.7 wt % of 1-hexadecene, and trace amounts of 1-octene and 1-decene) at a feeding rate of 3.3 moles per hour, bisCpZrCl$_2$ (dissolved or dispersed in toluene at a concentration of 1.4 wt %) at a feeding rate of 0.0048 mole per hour, and MAO (dissolved or dispersed in toluene at a concentration of 10 wt % at a feeding rate of 0.022 mole aluminum atoms per hour, operating at a constant temperature of 70° C. and residence time of 8.0 hours. The product mixture effluent exiting the reactor was immediately quenched by injecting room-temperature water at a feeding rate of 2 milliliter per hour. Filter aid was then added into the quenched product mixture. The resultant mixture was then filtered to remove solids to obtain a liquid. The liquid was then measured by gas chromatography to show a conversion of 1-tetradecene in the reaction of 71%. The liquid was then vacuum distilled at an absolute pressure of 4 mmHg (533 Pascal) to obtain a clear residual liquid as the final product. The final product was then characterized by gas chromatography to show the following composition, with total concentration of dimers at 98.84 wt %.

| | Components | Concentration (wt %) |
|---|---|---|
| | C14 monomer | <0.10 |
| Dimers | C16-C26 | 1.69 |
| | C28-C32 | 97.15 |
| | C16-C32 | 98.84 |
| Trimers (C36-C48) | | 0.86 |
| Tetramers (C48-C64) | | 0.24 |

The final product was then characterized by 41 NMR. Data show that the final product was predominantly 13-methyleneheptacosane. Data showed the presence of vinyls, vinylidenes, 1,2-di-substituted vinylenes, and tri-substituted vinylenes. The vinyls are attributed to residual 1-tetradecene monomer. The remaining olefin types (1,2-di-substituted vinylenes, tri-substituted vinylenes, and vinylidenes) were normalized to sum up to 100%. Their respective distributions are given below:

| Olefin Type | Concentration (mol %) |
|---|---|
| 1,2-Di-substituted Vinylenes | 1.1 |
| Tri-substituted Vinylenes | 1.1 |
| Vinylidenes | 97.8 |

Clearly, in the CSTR process of this Example 1, a high-purity, predominantly vinylidene olefin dimer product was produced. Because of the low concentrations of heavy components such as trimers and tetramers, the final product can be used as a vinylidene olefin dimer for many applications without further distillation to remove the heavy components. The overall conversion of the monomer at 71% without recycle is quite high. The very low distribution of 1,2-di-substituted vinylenes and tri-substituted vinylenes in the final product indicates that isomerization of the vinylidene olefin dimer into either of the vinylenes occurred at an extremely low level, if at all. This is due in part to the lack of metal elements other than aluminum and zirconium that may function as a Lewis acid capable of catalyzing the isomerization of vinyls and vinylidenes to produce vinylenes. As discussed below, it is believed that the presence of metal ions such as $Cu^{2+}$ in the reaction system, which can serve as Lewis acids, can lead to dimerization of the terminal olefin through mechanism different from that catalyzed by a metallocene compound, resulting in the production of vinylenes and branched oligomers, which is highly undesirable.

Example 2 (Comparative): Dimerization of 1-Tetradecene in a Batch Reactor

Into a 2-gallon (6.56-liter) batch reactor equipped with mechanical stirring was charged 2.2 grams (0.0076 moles) bisCpZrCl$_2$ (dissolved or dispersed in toluene at a concentration of 1 wt %), followed by 1.74 grams of MAO (corresponding to 0.030 moles of aluminum atoms) dissolved or dispersed in toluene at a concentration of 10 wt %, and lastly added 4.4 kilograms (22.4 moles) of 1-tetradecene feed (containing 98.6 wt % 1-tetradecene, 0.7 wt % 1-dodecene and 0.7 wt % of 1-hexadecene, and trace amounts of 1-octene and 1-decene) over a period of 90 minutes. The reactor was then operated at a constant reaction temperature of 70° C. for a batch reaction period of 6.0 hours. The product mixture at the end of the reaction period was immediately quenched by injecting 3 grams of water. Filter aid was then added into the quenched product mixture. The resultant mixture was then filtered to remove solids to obtain a liquid. The liquid was then measured by gas chromatography to show a conversion of 1-tetradecene in the reaction to oligomers of 37%. The liquid was then vacuum distilled at an absolute pressure of 10 mmHg (1333 Pascal) to remove residual monomer and to obtain a clear residual liquid as the final product. The final product was then characterized by gas chromatography to show the following composition, with a total concentration of dimers at 95.42 wt %:

| | Components | Concentration (wt %) |
|---|---|---|
| Dimers | C16-C26 | 2.19 |
| | C28-C30 | 93.23 |
| | C16-C30 | 95.42 |
| Trimers (C36-C48) | | 3.26 |
| Tetramers (C48-C64) | | 1.32 |

In the batch process of this comparative Example 2, the conversion of the linear terminal olefin monomer was much lower than in the continuous process of Example 1, even though the overall loading of the metallocene compound and MAO were comparable. In addition, the final product after the removal of residual monomer resulting from this batch process also contained trimers and tetramers at concentrations more than twice that in the final product from the continuous process of Example 1. The continuous process of Example 1 was far superior in producing a high-purity vinylidene olefin dimer product from a linear terminal olefin such as 1-tetradecene.

Example 3 (Comparative): Dimerization of 1-Tetradecene in a Batch Reactor

This experiment was carried out in substantially the same manner and sequence as in comparative Example 2, with the exception that the monomer feed was added first, followed by the addition of MAO solution at the same quantity and a holding period of 1 hour, before the metallocene compound solution at the same quantity was finally added. Catalyst loadings, temperature and reaction time remained the same as in Example 2. The conversion of monomer to oligomer product was measured to be 59%, slightly higher than Example 2, but still much lower than in Example 1. The final product was measured to have the following composition:

| | Components | Concentration (wt %) |
|---|---|---|
| Dimers | C16-C26 | 1.65 |
| | C28-C30 | 84.42 |
| | C16-C30 | 86.07 |
| Trimers (C36-C48) | | 6.25 |
| Tetramers (C48-C64) | | 7.68 |

In this batch process of comparative Example 3, selectivity of the terminal olefin toward dimers in the reaction was reduced to a mere 86.07%, resulting in large quantities of trimers and tetramers in the final product, which would have to be removed by distillation in order for the dimer to be useful as a pure product for many applications.

Example 4 (Comparative): Dimerization of 1-Decene in a Batch Reactor

Into a 2-gallon (6.56-liter) batch reactor equipped with mechanical stirring was charged 5 kilograms (26 moles) of 1-decene feed (containing 98.8 wt % 1-decene, 0.5 wt % 1-octene, 0.7 wt % 1-dodecene, and trace amounts of 1-hexene and 1-tetradecene), followed by 5 grams MAO (corresponding to 0.086 moles Al atoms) dissolved or dispersed in toluene at a concentration of 10 wt %, and finally 6.3 grams (0.022 moles) bisCpZrCl$_2$ dissolved or dispersed in toluene at a concentration of 1.4 wt %, and held at a constant reaction temperature of 80° C. for a batch reaction period of 6.0 hours. The product mixture at the end of the reaction period was immediately quenched by injection of 10 grams of water. Filter aid was then added into the quenched product mixture. The resultant mixture was then filtered to remove solids to obtain a liquid. The liquid was then measured by gas chromatography to show a conversion of monomers in the reaction to oligomers of 77%. The liquid was then distilled under a vacuum of an absolute pressure of 10 mmHg (1333 Pascal) to remove residual monomer and to obtain a clear residual liquid as an intermediate product. The intermediate product was then characterized by gas chromatography to show the following composition:

| Components | Concentration (wt %) |
| --- | --- |
| C20 Dimers | 79.23 |
| C30 Trimer | 4.72 |
| C40 Tetramer | 16.05 |

In the batch process of this comparative Example 4, the conversion of the linear terminal olefin monomer was much lower than in the continuous process of Example 1, even though the overall loading of the metallocene compound and MAO were comparable. In addition, the intermediate product after the removal of residual monomer resulting from this batch process also contained trimers and tetramers at a concentration more than ten times that in the final product from the continuous process of Example 1. Such large quantity of trimer and tetramers render the intermediate product not useable directly as a dimer product for many applications. The continuous process of Example 1 was far superior in producing a high-purity vinylidene olefin dimer product from a linear terminal olefin.

A further step of distillation of the intermediate product was then performed to remove the heavy trimer and tetramer to obtain a final product of C20 dimer having the following composition as measured by gas chromatography:

| Component | Concentration (wt %) |
| --- | --- |
| C20 dimer | 99.36 |
| C30 trimer | 0.56 |
| C40 tetramer | 0.08 |

The final product in this example was characterized by 1H-NMR to determine the distribution of olefin types. Vinyls were quantified from the NMR spectra but assumed to be from residual monomer. The distribution of vinylidenes, 1,2-di-substituted vinylenes and tri-substituted vinylenes in the oligomers are as follows:

| Components | Concentration (mol %) |
| --- | --- |
| 1,2-Di-substituted Vinylenes | 1.2 |
| Tri-substituted Vinylenes | 0.7 |
| Vinylidenes | 98.1 |

Thus, in the batch process of this Example 4, exceedingly low distribution of 1,2-di-substituted vinylene and tri-substituted vinylene were produced. Without intending to be bound by a particular theory, it is believed that this is due to the lack of metal ions and Lewis acids other than the MAO and the metallocene compounds in the reaction system, and the hence the lack of isomerization of the terminal olefin monomer and the vinylidene olefin dimer that may be otherwise catalyzed by the presence of other Lewis acids.

U.S. Pat. No. 4,658,078 disclosed multiple examples in which a 1-olefin (such as propylene, 1-hexene, and 1-octene) was oligomerized in the presence of bisCpZrCl$_2$ and MAO to produce a dimer product with impressive selectivity toward dimers. Many examples in this patent reference showed significant isomerization of the 1-olefin to produce its isomer 2-olefin. No distribution data of the vinylidenes, 1,2-di-substituted vinylenes and tri-substituted vinylenes in the final product were given in the examples in this patent. The high level of isomerization of the 1-olefin indicates that there is a high likelihood that the vinylidene olefin dimer and higher oligomers isomerized to form 1,2-di-substituted vinylenes and tri-substituted vinylenes at significant quantities. The cause of the isomerization is highly likely the presence of CuSO$_4$ in the reaction systems, which was derived from the CuSO$_4$.5H$_2$O used for making the MAO. The Cu$^{2+}$ in CuSO$_4$, a Lewis acid, catalyzed the isomerization of the 1-olefin to form 2-olefin isomer, the isomerization of vinylidene oligomers to form 1,2-di-substituted vinylenes and tri-substituted vinylenes, and likely the polymerization of the 1-olefins by mechanism different from that catalyzed by bisCpZrCl$_2$, again resulting in the formation of 1,2-di-substituted vinylenes and tri-substituted vinylenes.

None of the examples in U.S. Pat. No. 4,658,078 used a continuous process.

What is claimed is:

1. A continuous process for making a vinylidene olefin dimer from a terminal olefin comprising at least eight (8) carbon atoms per molecule, comprising:
   feeding a monomer stream comprising the terminal olefin into a reactor at a first feeding rate of R(to) moles of the terminal olefin per hour;
   feeding a metallocene compound having a formula Cp(Bg)$_n$MX$_2$Cp' into the reactor at a second feeding rate of R(mc) moles of the metallocene compound per hour, wherein M is selected from Hf and Zr; each X is independently a halogen or a hydrocarbyl group; Cp and Cp', the same or different, independently represents a cyclopentadienyl, alkyl-substituted cyclopentadienyl, indenyl, alkyl-substituted indenyl, 4,5,6,7-tetrahydro-2H-indenyl, alkyl-substituted 4,5,6,7-tetrahydro-2H-indenyl, 9H-fluorenyl, and alkyl-substituted 9H-fluorenyl; each Bg is a bridging group covalently linking Cp and Cp'; and n is 0, 1, or 2;
   feeding an alumoxane feed into the reactor at a third feeding rate corresponding to R(Al) moles of aluminum atoms per hour, wherein the alumoxane feed comprises metal elements other than aluminum, alkali metals, alkaline earth metals, and the metal contained in the metallocene compound at a total concentration no greater than 50,000 ppm by mole, based on the total moles of all metal atoms present in the alumoxane feed;

conducting oligomerization reaction in the reactor at a temperature in the range from 50 to 90° C., wherein the oligomerization reaction has a conversion of the terminal olefin of no less than 70%;

drawing a stream of oligomerization reaction mixture from the reactor comprising unreacted terminal olefin, a dimer of the terminal olefin, and a trimer of the terminal olefin, wherein:

the first feeding rate, the second feeding rate, and the third feeding rate are chosen such that:

$$350<R(to)/R(mc)\leq 750,$$

$$2\leq R(Al)/R(mc)\leq 10,$$

the oligomerization reaction has a selectivity of the terminal olefin toward trimer no greater than 5% and the oligomerization reaction has a selectivity of the terminal olefin toward dimers of at least 95%; wherein the dimers comprise the vinylidene olefin dimer.

2. The process of claim 1, wherein both Cp and Cp' are cyclopentadienyl, and n is zero.

3. The process of claim 1, wherein in the metallocene compound, M is Zr.

4. The process of claim 1, wherein in the metallocene compound, X is Cl.

5. The process of claim 1, wherein the alumoxane is methyl alumoxane.

6. The process of claim 1, wherein $$600<R(to)/R(mc)<750.$$

7. The process of claim 1, wherein:

$$2\leq R(Al)/R(mc)\leq 5.$$

8. The process of claim 1, wherein:
the oligomerization reaction has a selectivity of the terminal olefin toward the trimer of no greater than 3%.

9. The process of claim 1, wherein:
the oligomerization reaction has a selectivity of the terminal olefin toward vinylidene oligomers of at least 95%.

10. The process of claim 9, wherein:
the oligomerization reaction has a selectivity of the terminal olefin toward vinylidene oligomers of at least 98%.

11. The process of claim 1, wherein:
the oligomerization reaction has a selectivity of the terminal olefin toward internal olefin oligomers of at most 5%.

12. The process of claim 11, wherein:
the oligomerization reaction has a selectivity of the terminal olefin internal olefin oligomers of at most 2%.

13. The process of claim 1, wherein:
The oligomerization reaction has a selectivity of the terminal olefin toward tri-substituted oligomers of at most 5%.

14. The process of claim 13, wherein:
the oligomerization reaction has a selectivity of the terminal olefin toward tri-substituted oligomers of at most 2%.

15. The process of claim 1, wherein the oligomerization reaction has a selectivity of the terminal olefin toward dimers of at least 97.5%.

16. The process of claim 1, further comprising:
quenching the stream of oligomerization reaction mixture using a quenching agent.

17. The process of claim 1, further comprising:
obtaining a recycle stream comprising the unreacted terminal olefin from the oligomerization reaction mixture; and
recycling the recycle stream of the unreacted terminal olefin to the reactor as a portion of the monomer stream.

18. The process of claim 1, wherein:
the monomer stream comprises one or more of linear terminal olefins selected from 1-octene, 1-decene, 1-dodecene, 1-tetradecene, 1-hexadecene, 1-octadecene, and 1-icosene.

19. The process of claim 18, wherein:
the monomer stream consists essentially of one linear terminal olefin selected from selected from 1-octene, 1-decene, 1-dodecene, 1-tetradecene, 1-hexadecene, 1-octadecene, and 1-icosene.

20. The process of claim 1, further comprising:
obtaining a dimer product consisting essentially of the dimer of the terminal olefin from the stream of the oligomerization reaction mixture without a step of removing the trimer.

21. The process of claim 1, which is carried out in a continuously stirred tank reactor.

22. The process of claim 1, further comprising feeding an inert solvent into the reactor.

23. The process of claim 1, wherein the oligomerization reaction has a selectivity of the terminal olefin toward dimers of at least 98%.

* * * * *